United States Patent [19]

Böshagen et al.

[11] Patent Number: 4,670,423
[45] Date of Patent: Jun. 2, 1987

[54] MONOSILYLATED AMINOPHENYLETHYLAMINE DERIVATIVES, A PROCESS FOR THEIR PREPARATION, AND THEIR USE FOR PROMOTING GROWTH

[75] Inventors: Horst Böshagen; Jürgen Stoltefuss, both of Haan; Friedrich Berschauer, Wuppertal; Anno de Jong, Wuppertal; Martin Scheer, Wuppertal, all of Fed. Rep. of Germany

[73] Assignee: Bayer Aktiengesellschaft, Leverkusen, Fed. Rep. of Germany

[21] Appl. No.: 709,624

[22] Filed: Mar. 8, 1985

[30] Foreign Application Priority Data

Mar. 14, 1984 [DE] Fed. Rep. of Germany ....... 3409270

[51] Int. Cl.$^4$ .................. A61K 31/695; A61C 23/00; C07F 7/10
[52] U.S. Cl. ...................................... 514/63; 556/413; 556/423; 556/415; 556/424; 546/14; 548/406;
[58] Field of Search ............... 556/413, 423, 415, 424; 548/406; 260/239 R, 239 A; 514/63

[56] References Cited

U.S. PATENT DOCUMENTS 3,171,851  3/1965  Pepe .................................... 556/413

FOREIGN PATENT DOCUMENTS 0026298  8/1980  European Pat. Off. ............ 556/413
0104888  9/1984  European Pat. Off. ............ 556/413
1668982  9/1971  Fed. Rep. of Germany ...... 556/413

OTHER PUBLICATIONS

Arnzeim-Forsch., 23, No. 5, 1972, pp. 861–869.

Primary Examiner—Paul F. Shaver
Attorney, Agent, or Firm—Sprung Horn Kramer & Woods

[57] ABSTRACT

Monosilylated aminophenylethylamine derivative of the formula

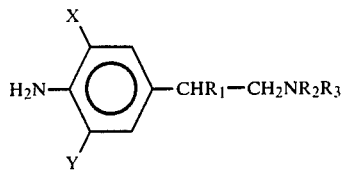

in which
X and Y each independently is hydrogen or halogen,
$R_1$ is the radical

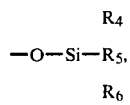

$R_2$ is hydrogen or an aliphatic hydrocarbon radical having up to 10 C atoms,
$R_3$ is hydrogen, an aliphatic hydrocarbon radical which can optionally be substituted by halogen, a phenyl radical which can optionally be substituted by halogen, hydroxyl, alkyl, aryl, alkoxy, alkylthio, optionally substituted phenoxy, optionally substituted phenylthio, cyano or trifluoromethyl, or a heterocyclic radical, or, together with $R_2$ is a nitrogen-containing saturated heterocyclic radical, and
$R_4$, $R_5$ and $R_6$ each independently is an alkyl radical, or physiologically tolerated salts thereof, promote the growth of animals.

12 Claims, No Drawings

MONOSILYLATED AMINOPHENYLETHYLAMINE DERIVATIVES, A PROCESS FOR THEIR PREPARATION, AND THEIR USE FOR PROMOTING GROWTH

The present invention relates to monosilylated aminophenylethylamine derivatives, a process for their preparation, and their use in animal nutrition for increasing growth and for improving the flesh/fat ratio.

The use of feed additives for achieving greater increases in growth and improved feed utilization is already a widespread practice in animal nutrition, particularly in the fattening of pigs, cattle and poultry.

The new monosilylated aminophenylethylamine derivatives of the general formula (I)

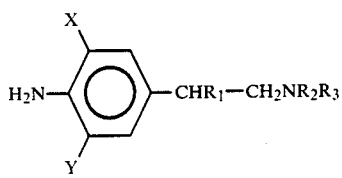

in which
X and Y are identical or different and represent hydrogen or halogen,
$R_1$ represents the radical

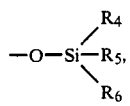

$R_2$ denotes hydrogen or a straight-chain, branched, saturated or unsaturated alkyl radical having up to 10 C atoms,
$R_3$ denotes hydrogen or a straight-chain, branched, saturated or unsaturated alkyl radical which can be substituted by halogen, preferably chlorine and/or fluorine, or denotes a phenyl radical which can optionally be substituted by halogen, hydroxyl, alkyl, aryl, alkoxy, alkylthio, optionally substituted phenoxy or phenylthio, cyano or trifluoromethyl or denotes a heterocyclic radical, or, together with $R_2$, denotes a nitrogen-containing saturated heterocyclic radical, such as, for example, azabicyclononane, substituted azabicyclononane, azabicyclooctane and the like, and $R_4$, $R_5$ and $R_6$ denote a straight-chain or branched alkyl radical,
and their physiologically tolerated salts have been found.

The substances possess excellent growth-promoting actions and furthermore improve the flesh/fat ratio in favor of flesh.

Preferred compounds are phenylethylamine derivatives of the general formula (I), in which
X and Y represent chlorine,
$R_2$ denotes a saturated or unsaturated, branched or straight-chain alkyl radical having up to 6 C atoms, and
$R_3$ represents hydrogen,
or compounds of the formula (I),
in which
X and Y denote chlorine,
$R_2$ denotes hydrogen and
$R_3$ denotes either a straight-chain or branched, saturated or unsaturated $C_1$-$C_6$-alkyl radical which is substituted by one or more chlorine or fluorine atoms, or a phenyl radical which can optionally be substituted by halogen, hydroxyl, $C_1$-$C_4$-alkyl, $C_1$-$C_4$-alkoxy, $C_6$-$C_{10}$-aryl or $C_1$-$C_4$-alkylthio or by optionally substituted phenoxy or phenylthio,
and their physiologically tolerated salts.

Particularly preferred compounds are phenylethylamine derivatives of the formula (I),
in which
X and Y represent chlorine,
$R_1$ represents $OSi(CH_3)_2CH(CH_3)CH(CH_3)_2$, $R_2$ represents a saturated or unsaturated, branched or straight chain alkyl radical having up to 6 C atoms and
$R_3$ represents hydrogen,
and their physiologically tolerated salts.

The new compounds of the formula (I)

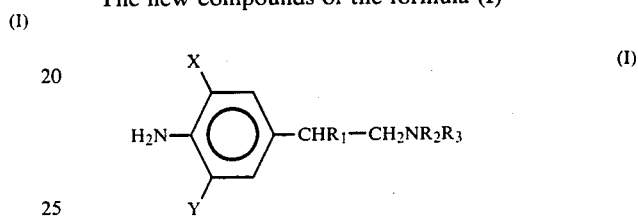

in which
X and Y are identical or different and represent hydrogen or halogen,
$R_1$ represents the radical

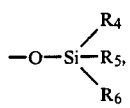

$R_2$ denotes hydrogen or a straight-chain, branched, saturated or unsaturated alkyl radical having up to 10 C atoms,
$R_3$ denotes hydrogen or a straight-chain, branched, saturated or unsaturated alkyl radical which is substituted by halogen, preferably chlorine and/or fluorine, or denotes a phenyl radical which can optionally be substituted by halogen, hydroxyl, alkyl, aryl, alkoxy, alkylthio, optionally substituted phenoxy or phenylthio, cyano or trifluoromethyl, or denotes a heterocyclic radical or, together with $R_2$, denotes a nitrogen-containing saturated heterocyclic radical, such as, for example, azabicyclononane, substituted azabicyclononane, azabicyclooctane and the like, and $R_4$, $R_5$ and $R_6$ denote a straight-chain or branched alkyl radical,
and their physiologically tolerated salts are obtained by a method in which compounds of the general formula (II)

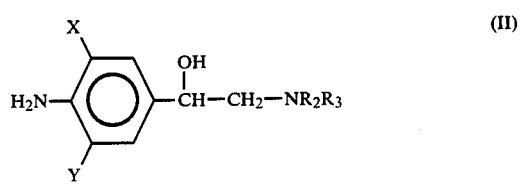

either as a racemate or as one of the enantiomeric forms,
in which

X, Y, $R_2$ and $R_3$ have the meaning given above, are reacted with suitable silylating agents of the formula (III)

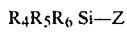  (III)

in which

Z denotes halogen, CN, $-O-SO_2-CF_3$, $-O-SiR_4R_5R_6$ or $-O-SO_2-O-SiR_4R_5R_6$, and $R^4$, $R^5$ and $R^6$ have the meaning given above.

The starting compounds of the formulae (II) and (III) are either known or can be prepared by known methods (see, for example, R. E. Lutz and Co-workers, J. Org. Chem. 12, 617–703 (1974)).

The process according to the invention can be carried out in the presence of diluents. Suitable diluents are all inert organic solvents. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl eter, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, benzonitrile and glutarodinitrile, amides, such as, for example, dimethylformamide, dimethylacetamide and N-methylpyrrolidone, and dimethyl sulphoxide, tetramethylene sulphone and hexamethylphosphoric acidtriamide.

The process according to the invention can be carried out in the presence of catalysts. Preferably used catalysts are: imidazole, triazole or diisopropylethylamine.

The reaction temperature is kept between about 0° C. and 130° C., preferably between about 20° C. and 100° C. The process is preferably carried out under atmospheric pressure.

The starting compounds of the formulae II and III are employed in general in about an equimolar ratio. An excess of 10–200% of the compounds of the formula III is preferred.

Working-up after the reaction is complete is carried out in a manner which is known per se.

The following stock animals and pets may be mentioned as examples of animals for which the active compounds can be used for promoting and accelerating growth and for improving feed utilization: warm-blooded animals, such as cattle, pigs, horses, sheep, goats, cats, dogs, rabbits, fur-bearing animals, for example mink and chinchillas, poultry, for example chickens, geese, ducks, turkeys, pigeons, parrots and canaries, and cold-blooded animals, such as fish, for example carp, and reptiles, for example snakes.

The amounts of active compounds which are administered to the animals to achieve the desired effect can be varied substantially owing to the advantageous properties of the active compounds. It is preferably about 0.01 to 50, in particular 0.1 to 10, mg/kg of body weight daily. The period of administration can be from a few hours or days up to several years. The appropriate amount of active compound and the appropriate period of administration depend, in particular, on the species, age, sex, state of health and nature of keeping and feeding of the animals, and can easily be determined by any expert.

The active compounds are administered to the animals by the customary methods. The nature of the administration depends, in particular, on the species, the behavior and the state of health of the animals. Thus, administration can be effected orally or parenterally, once or several times daily at regular or irregular intervals.

The active compounds according to the invention are particularly suitable for parenteral use, and they are converted to a usable formulation with suitable, preferably non-aqueous tolerated solvents or diluents.

Suitable formulating agents are preferably physiological vegetable products, such as, for example, sesame oil, groundnut oil or corn germ oil. These oils or other synthetic triglycerides, such as, for example, Miglycol ® or Myritol ® can be thickened by suitable additives, such as, for example, hardened castor oil or Al monostearate. By means of such combinations, the viscosity and hence the depot effect can be varied within wide limits.

Implants made of silicone or high molecular weight polyglycols or other physiologically tolerated polymers are also possible.

For reasons of expediency, oral administration, in particular in the rhythm of the intake of food and/or drink by the animals, is frequently to be preferred.

The active compounds can be administered as a mixture of pure substances or in the formulated form, that is to say mixed with non-toxic inert carriers of any kind, for example, with carriers and in formulations as are customary in the case of nutritive preparations.

The active compounds, optionally in the formulated form, can also be administered in a suitable form together with pharmaceutical active compounds, mineral salts, trace elements, vitamins, proteins, fats, colorants and/or flavoring agents.

Oral administration together with the need and/or drinking water is recommended, the active compounds being added to the total amount or only portions of the feed and/or drinking water as required.

In the case of oral administration, the compounds can be admixed to the feed and/or drinking water in accordance with customary methods by simple mixing as pure substances, preferably in the finely divided form or in the formulated form mixed with edible nontoxic carriers, and optionally in the form of a premix or a feed concentrate.

The feed and/or drinking water can contain the active compounds in a concentrations (w/w) of, for example, about 0.01 to 50 ppm, in particular 0.1 to 10 ppm. The optimum level of the concentration of the active compounds in the feed and/or drinking water depends, in particular, on the amount of feed and/or drinking water taken in by the animals and can easily be determined by any expert.

In the case of parenteral administration, the optimum dose depends, in particular, on the frequency of administration, on the animal species and on the age and weight of the animals.

The nature of the feed and its composition is irrelevant. All the customary or specific feed compositions, which preferably contain the customary equilibrium of energy substances and builder substances, including vitamins and mineral substances, necessary for balanced nutrition, can be used. The feed can be composed, for example, of vegetable substances, for example, hay, beet, cereals and cereal by-products, animal substances, for example, meat, fats and bone meal, fish products, vitamins, for example vitamin A, D complex and B complex, proteins, aminoacids, for example DL-methionine, and inorganic substances, for example lime and sodium chloride.

Feed concentrates contain the active compounds alongside edible substances, for example rye flour, corn flour, soy bean flour or lime, optionally with further nutrients and builder substances, as well as proteins, mineral salts and vitamins. They can be prepared by the customary mixing methods.

In premixes and feed concentrates, preferably, the active compounds can optionally also be protected from air, light and/or moisture by suitable agents which coat its surface, for example with non-toxic waxes or gelatine.

The following is an example of the composition of a feed for rearing chicks, which contains an active compound according to the invention: 200 g of wheat, 340 g of corn, 361 g of coarse soy bean meal, 60 g of beef tallow, 15 g of dicalcium phosphate, 10 g of calcium carbonate, 4 g of iodinated sodium chloride, 7.5 g of a vitamin/mineral mixture and 2.5 g of an active compound premix give, after careful mixing, 1 kg of feed.

One kg of feed mixture consists of: 600 I.U. of vitamin A, 100 I.U. of vitamin $D_3$, 10 mg of vitamin E, 1 mg of vitamin $K_3$, 3 mg of riboflavin, 2 mg of pyridoxine, 20 mcg of vitamin $B_{12}$, 5 mg of calcium pantothenate, 30 mg of nicotinic acid, 200 mg of choline chloride, 200 mg of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains the active compounds in the desired amount, for example 10 mg, and also 1 g of DL-methionine as well as an amount of soy bean flour such that 2.5 g of premix are formed.

The following is an example of the composition of a feed for rearing pigs, which contains the active compound according to the invention: 630 g of shredded cereal feed (composed of 200 g of corn 150 g of shredded barley, 150 g of shredded oats and 130 g of shredded wheat), 80 g of fish meal, 60 g of coarse soy bean meal, 60 g of tapioca meal, 38 g of brewers' yeast, 50 g of a vitamin/mineral mixture for pigs (composition, for example, as for the chick feed), 30 g of linseed cake meal, 30 g of oorn gluten feed, 10 g of soy bean oil, 10 g of sugar cane molasses and 2 g of an active compound premix (composition, for example, as for the chick feed) give, after careful mixing, 1 kg of feed.

The feed mixtures indicated are intended preferably for rearing and fattening chicks or pigs respectively, but they can be used, in the same or a similar composition, on for rearing and fattening other animals.

Several investigations into feeding and metabolism were carried out with the active compounds according to the invention.

The following results were obtained:

EXAMPLE 1a

| a Animal characteristics and feed | |
|---|---|
| a 1 | Rats, female | |
| a 2 | Number | 15 |
| a 3 | Breed | SPF Wistar, Hagemann breed |
| a 4 | Weight | 150-200 g |
| a 5 | Condition | good |
| a 6 | Feed | |
| | crude nutrients* | |
| | crude protein | 19.0 |

-continued

| a Animal characteristics and feed | |
|---|---|
| crude fat | 4.0 |
| crude fiber | 6.0 |
| Ash | 7.0 |
| Water | 13.5 |
| N—free extract material | 50.5 |
| Metabolizable energy | |
| Kcal/kg | 3100 |
| KJ/kg | 13,000 |
| Mineral substances* | |
| Calcium | 0.9 |
| Phosphorus | 0.7 |
| Magnesium | 0.2 |
| Sodium | 0.2 |
| Vitamins** | |
| Standard diet | |
| Vitamin A | 15,000 I.U. |
| Vitamin $D_3$ | 600 I.U. |
| Vitamin E | 75 mg |
| Vitamin $K_3$ | 3 mg |
| Vitamin $V_1$ | 18 mg |
| Vitamin $B_2$ | 12 mg |
| Vitamin $B_6$ | 9 mg |
| Vitamin $B_{12}$ | 24 mcg |
| Nicotinic acid | 36 mg |
| Pantothenic acid | 21 mg |
| Folic acid | 2 mg |
| biotin | 60 mg |
| choline | 600 mg |
| Vitamin C | 36 mg |
| Aminoacids* | |
| lysine | 0.9 |
| methionine + cystine | 0.6 |
| phenylalanine + tyrosine | 1.4 |
| arginine | 1.1 |
| histidine | 0.4 |
| tryptophan | 0.2 |
| threonine | 0.6 |
| isoleucine | 0.9 |
| leucine | 1.3 |
| valine | 0.9 |
| Trace elements** | |
| magnanese | 75.0 |
| iron | 135.0 |
| copper | 13.0 |
| zinc | 70.0 |
| iodine | 0.9 |
| fluorine | 9.0 |

*% in the diet (mean value)
**mg in 1 kg of diet (mean value)

(b) Treatment of the animals

The animals were accustomed for 2 days to the new keeping conditions, the experimental feed being administered in general without added active compound. On the third day of the experiment, the animals were randomized, and the test groups were then formed so that both the mean values and the scatters in the body weights were the same from group to group. A preliminary period of 5 days was followed by a main period of 17 days, in which feed intake, additional growth and feed utilization were determined.

The following treatments were tested:

| | | | | |
|---|---|---|---|---|
| b 1 | Negative control (n = 10) | | | |
| b 2 | 25 ppm (active compound from Example 1) (n = 5) | | | |
| c | Result (feed intake, growth, feed utilization) during the main period (17 days) | | | |
| | | Feed intake (g) | Additional growth (g) | Feed utilization (g/g) |
| c 1 | Negative control | 226 | 39.1 | 6.80 |
| c 2 | 25 ppm (active compound from | 320 | 58.6 | 5.46 |

EXAMPLE 1b

| | a Animal characteristics and feed | |
|---|---|---|
| a 1 | Rats, female | |
| a 2 | Number | 15 |
| a 3 | Breed | SPF Wistar, Hagemann breed |
| a 4 | Weight | 200–235 g |
| a 5 | Condition | good |
| a 6 | Feed | as in Example 1a |

(b) Treatment of the animals

The animals were accustomed for 2 days to the new keeping conditions, the experimental feed being administered in general without added active compound. On the third day of the experiment, the animals were randomized, and the test groups were then formed so that both the mean values and the scatters in the body weights were the same from group to group. A preliminary period of 5 days was followed by a main period of 17 days, in which feed intake, additional growth and feed utilization were determined.

The following treatments were tested:

| b 1 | Negative control (n = 10) | | | |
|---|---|---|---|---|
| b 2 | 0.2 ppm (active compound from Example 1) (n = 5) | | | |
| c | Result (feed intake, growth, feed utilization) during the main period (17 days) | | | |
| | | Feed intake (g) | Additional growth (g) | Feed utilization (g/g) |
| c 1 | Negative control | 291 | 23.9 | 12.17 |
| c 2 | 0.25 ppm (active compound from Example 1) | 350 | 42.7 | 8.20 |

Preparation examples

EXAMPLE 1

N-[2-(4-Amino-3,5-dichloro-phenyl)-2-(1,2-dimethyl-propyl-dimethyl-silyloxy)-ethyl]-N-t-butylamine

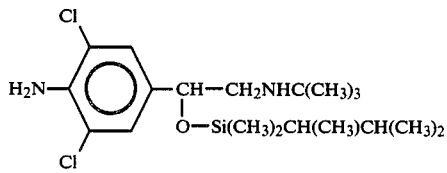

2.04 g (30 mmol) of imidazole are added to 2.77 g (10 mmol) of 1-(4-amino-3,5-dichloro-phenyl)-2-(t-butylamino)-ethanol in 50 ml of absolute dimethylformamide, and 3.64 g (22 mmol) of dimethyl-isoamyl-silyl chloride are added dropwise to the stirred mixture. When the slightly exothermic reaction has died down, stirring is continued for a further hour at room temperature, after which the dimethylformamide is stripped off in vacuo, 50 ml of water is added to the syrupy residue, and the mixture is extracted with 3×50 ml of toluene. The toluene extract is thoroughly washed 3× with water, dried with magnesium sulphate and evaporated down in vacuo. The remaining pale yellow syrup is then subjected to a high vacuum (0.01 mm Hg) for 2 hours. 4.02 g (99% of theory) of a pale yellow oil. The product is pure according to gas chromatography.

$R_f$ value: 0.76.

(TLC aluminum foil (Merck), silica gel 60 $F_{254}$; mobile phase: 1:1 toluene/ethanol).

IR (CHCl$_3$) cm$^{-1}$:3495; 3403; 2961 (s); 2871 (m); 1620 (m); 1582; 1485 (s); 1414; 1399; 1366 (m); 1291; 1254 (s); 1226; 1091 (s); 975 (m); 925; 904; 874; 837 (s).

The following compounds were prepared as described above:

EXAMPLE 2

N-[2-(4-Amino-3,5-dichloro-phenyl)-2-(1,2-dimethyl-propyl-dimethylsilyloxy)-ethyl]-N-isopropylamine

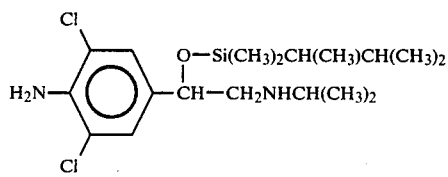

Yield: 70% of theory. Pale yellow oil. Pure according to gas chromatography.

$R_f$ value: 0.68

(TLC aluminum foil (Merck), silica gel 60 $F_{254}$; mobile phase: 1:1 toluene/ethanol).

IR (CHCl$_3$) cm$^{-1}$:3501; 3401; 2963 (s); 2871 (s); 1620 (m); 1582 (m); 1487 (s); 1415; 1385; 1346; 1292; 1254 (s); 1177; 1081 (s); 971; 920; 875 (m); 837 (s).

EXAMPLE 3

N-[2-(4-amino-3,5-dichloro-phenyl)-2-(1,2-dimethyl-propyldimethylsilyloxy)-ethyl]-N-(2,2-dimethyl)-propylamine

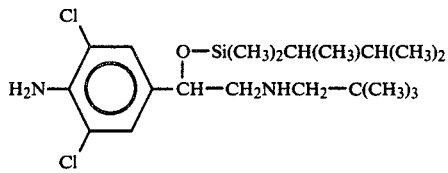

Yield: 78% of theory. Pale yellow oil. Pure according to gas chromatography.

$R_f$ value: 0.72

(TLC aluminum foil (Merck), silica gel 60 $F_{254}$; mobile phase: 3:1 toluene/ethanol).

IR (CHCl$_3$) cm$^{-1}$:3498; 3403; 2960 (s); 2871; 2829; 2355; 1619 (m); 1585 (m); 1563; 1486 (s); 1413; 1367 (m); 1291; 1254 (s); 1086 (a); 1010; 974; 928; 910 (m); 872; 837 (s); 728.

EXAMPLE 4

N-[2-(4-amino-3,5-dichloro-phenyl)-2-(1,2-dimethyl-silyloxy)-ethyl]-N-(1,1-dimethyl)-propylamin Yield: 86%, pale yellow oil, pure according to gas chromatography $R_f$ value: 0,81 (TLC-aluminium foil (Merck) silicagel 60 $F_{254}$; mobile phase 1:1 toluene/ethanol)

EXAMPLE 5

N-[2-(4-amino-3,5-dichloro-phenyl)-2-(t-butyl-dimethylsilyloxy)-ethyl]-N-t-butylamine

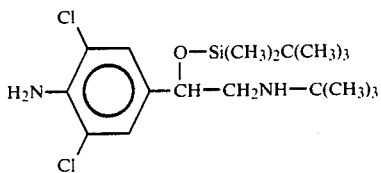

4.16 g (15 mmol) of 1-(4-amino-3,5-dichlorophenyl)2-butylamino)-ethanol are dissolved in 50 ml of absolute dimethylformamide, 3.06 g (45 mmol) of imidazole are added, and 4.97 g (33 mmol) of t-butyl-dimethylsilyl chloride are added dropwise, while stirring. The mixture is stirred for 1 hour at room temperature, for 1 hour at 60° C. and for 3 hours at 80° C. The solvent is then stripped off in vacuo, 50 ml of water were added to the residue, and the mixture is extracted 3×with 50 ml of toluene. The toluene extract is once again washed 3×with water, dried, and evaporated down in vacuo. The remaining syrup is chromatographed over 100 g of silica gel 60 (mobile phase: (1) toluene, (2) 30:1 toluene/EtOH). 5.3 g) 90% of theory of a chromatographically pure fraction are obtained in the form of a yellow oil.

$R_f$ value: 0.65

(TLC aluminium foil (Merck), silica gel 60 $F_{254}$; mobile phase: 3:1 toluene/ethanol).

It will be understood that the specification and examples are illustrative but not limitative of the present invention and that other embodiments within the spirit and scope of the invention will suggest themselves to those skilled in the art.

EXAMPLE 6

N-[2-(4-amino-3,5-dichloro-phenyl)-2-(1,2-dimethylpropyl-dimethylsilyloxy)-ethyl]-3-methyl-4-(4-trifluormethylmercapto-phenoxy)-anilin $R_f$ value: 0.86; mobile phase toluene /aceticacidester 6:1

We claim:

1. A monosilylated aminophenylethylamine derivative of the formula

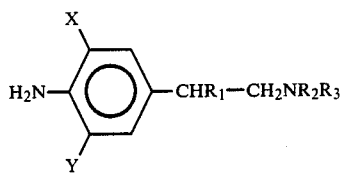

in which

X and Y each independently is hydrogen or halogen,
$R_1$ is the radical

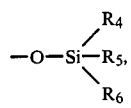

$R_2$ is hydrogen or an aliphatic hydrocarbon radical having up to 10 C atoms, $R_3$ is hydrogen, an aliphatic hydrocarbon radical which can optionally be substituted by halogen, a phenyl radical which can optionally be substituted by halogen, hydroxyl, alkyl, aryl, alkoxy, alkylthio, optionally substituted phenoxy, optionally substituted phenylthio, cyano or trifluoromethyl, or a heterocyclic radical, or, together with $R_2$ is a nitrogen-containing saturated heterocyclic radical, and $R_4$, $R_5$ and $R_6$ each independently is an alkyl radical, or a physiologically tolerated salt thereof.

2. A monosilylated aminophenylethylamine derivative or salt according to claim 1,
in which
X and Y each is chlorine,
$R_2$ is an aliphatic hydrocarbon radical having up to 6 C atoms, and
$R_3$ is hydrogen.

3. A monosilylated aminophenylethylamine derivative or salt according to claim 1,
in which
X and Y each is chlorine,
$R_2$ is hydrogen, and
$R_3$ is an aliphatic hydrocarbon radical containing up to 6 C atoms optionally substituted by chlorine or fluorine, or a phenyl radical optionally substituted by halogen, hydroxyl, $C_1$-$C_4$-alkyl, $C_1$-$C_4$-alkoxy, $C_6$-$C_{10}$-aryl-thio, $C_1$-$C_4$-alkyl-thio, optionally substituted phenoxy or optionally substituted phenylthio.

4. A monosilylated aminophenylethylamine derivative or salt according to claim 1,
in which
X and Y each is chlorine,
$R_2$ is hydrogen, and
$R_3$ is a phenoxyphenyl or phenylthiophenyl radical which is substituted by $CF_3S$, $CF_3SO_2$, $C_1$-$C_4$-alkyl, halogen and/or a phenyl radical.

5. A compound according to claim 1, wherein such compound is N-[2-(4-amino-3,5-dichloro-phenyl)-2-(1,2-dimethylpropyl-dimethyl-silyloxy)-ethyl]-N-t-butylamine of the formula

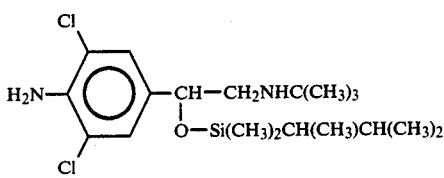

or a physiologically tolerated salt thereof.

6. A compound according to claim 1, wherein such compound is N-[2-(4-amino-3,5-dichloro-phenyl)-2-(1,2-dimethylpropyl-dimethylsilyloxy)-ethyl]-N-isopropylamine of the formula

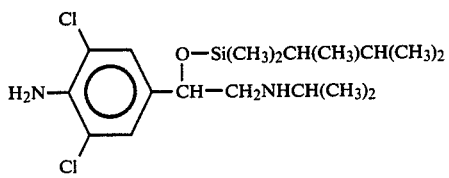

or a physiologically tolerated salt thereof.

7. A compound according to claim 1, wherein such compound is N-[2-(4-amino-3,5-dichloro-phenyl)-2-

(1,2-dimethylpropyl-dimethylsilyloxy)-ethyl]-N-(2,2-dimethyl)propylamine of the formula

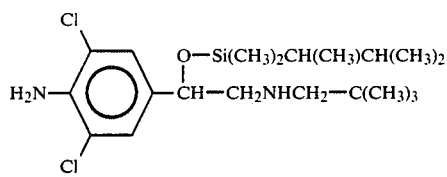

or a physiologically tolerated salt thereof.

8. A compound according to claim 1, wherein such compound is N-2-(4-amino-3,5-dichloro-phenyl)-2-(t-butyl-dimethylsilyloxy)-ethyl]-N-t-butylamine of the formula

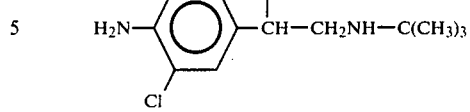

or a physiologically tolerated salt thereof.

9. An animal growth promoting composition comprising an amount of a compound or salt according to claim 1 effective to promote growth and a diluent.

10. A composition according to claim 9, wherein the diluent is edible.

11. A method of promoting the growth of an animal which comprises administering to such animal a growth promoting effective amount of a compound or salt according to claim 1.

12. The method according to claim 11, wherein such compound is
N-[2-(4-amino-3,5-dichloro-phenyl)-2-(1,2-dimethyl-propyl-dimethyl-silyloxy)-ethyl]-N-t-butylamine,
N-[2-(4-amino-3,5-dichloro-phenyl)-2-(1,2-dimethyl-propyl-dimethylsilyloxy)-ethyl]-N-isopropylamine,
N-2-(4-amimo-3 5-dichloro-phenyl)-2-(1,2-dimethylpropyl-dimethylsilyloxy]N-(2,2-dimethyl) propylamine or
N-2-(4-amino-3,5-dichloro-phenyl)-2-(t-butyldimethylsilyloxy)-ethyl]-N-t-butylamine
or a physiologically tolerated salt thereof.

* * * * *

UNITED STATES PATENT AND TRADEMARK OFFICE
CERTIFICATE OF CORRECTION

PATENT NO. : 4,670,423
DATED : June 2, 1987
INVENTOR(S) : Horst Böshagen, et al.

It is certified that error appears in the above-identified patent and that said Letters Patent is hereby corrected as shown below:

| | |
|---|---|
| Title Page, under "Foreign Patent Documents" | Line 1, delete "8/1980" and substitute --4/1981--; Line 2, delete "9/1984" and substitute --4/1984-- |
| Col. 2, line 61 | Delete ring in formula and substitute bonding lines as follows: 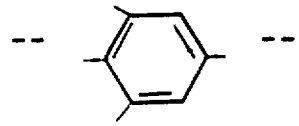 |
| Col. 4, line 37 | Delete "need" and substitute --feed-- |
| Col. 5, line 45 | Delete "oorn" and substitute --corn-- |
| Col. 8, line 64 | Before "silyloxy" insert --propyldimethyl-- |
| Col. 11, line 26; Col. 12, lines 26 and 29 | After "N-" insert --[-- |
| Col. 12, line 26 | Delete "3 5" and substitute --3,5-- |
| Col. 12, line 27 | After "dimethylsilyloxy" insert --)-ethyl]-- |

Signed and Sealed this

Eighth Day of March, 1988

Attest:

DONALD J. QUIGG

Attesting Officer     Commissioner of Patents and Trademarks